United States Patent
Langdon et al.

(10) Patent No.: US 9,398,985 B2
(45) Date of Patent: Jul. 26, 2016

(54) PRESTRAINED STRETCHED LAMINATES

(75) Inventors: Frederick Michael Langdon, Cincinnati, OH (US); Fred Naval Desai, Fairfield, OH (US)

(73) Assignee: The Procter & Gamble Company, Cincinnati, OH (US)

(*) Notice: Subject to any disclaimer, the term of this patent is extended or adjusted under 35 U.S.C. 154(b) by 656 days.

(21) Appl. No.: 12/813,727

(22) Filed: Jun. 11, 2010

(65) Prior Publication Data

US 2010/0318054 A1    Dec. 16, 2010

Related U.S. Application Data

(60) Provisional application No. 61/186,689, filed on Jun. 12, 2009.

(51) Int. Cl.
*A61F 13/15* (2006.01)
*B32B 37/00* (2006.01)
*A61F 13/49* (2006.01)

(52) U.S. Cl.
CPC ....... *A61F 13/4902* (2013.01); *A61F 13/15577* (2013.01); *A61F 13/15699* (2013.01); *A61F 13/15764* (2013.01); *A61F 2013/1591* (2013.01); *A61F 2013/15788* (2013.01); *A61F 2013/15796* (2013.01); *A61F 2013/15861* (2013.01); *A61F 2013/15878* (2013.01)

(58) Field of Classification Search
CPC ............... A61F 13/15577; A61F 13/15699; A61F 13/15861; A61F 13/15764; A61F 2013/15861; A61F 2013/15878; A61F 2013/1591; A61F 2013/15796; A61F 2013/15788

USPC ............... 604/367, 373, 372, 385.22, 385.27, 604/385.24; 156/73.1, 164, 163, 60, 264, 156/265

See application file for complete search history.

(56) References Cited

U.S. PATENT DOCUMENTS

| | | | |
|---|---|---|---|
| 6,096,668 A * | 8/2000 | Abuto et al. | 442/328 |
| 7,501,034 B2 | 3/2009 | Ashraf | |
| 8,236,121 B2 | 8/2012 | Ashraf | |
| 2004/0020579 A1 * | 2/2004 | Durrance et al. | 156/66 |
| 2004/0192140 A1 | 9/2004 | Schneider et al. | |
| 2004/0219854 A1 | 11/2004 | Groitzsch et al. | |
| 2004/0222553 A1 * | 11/2004 | Desai et al. | 264/171.24 |
| 2006/0083900 A1 | 4/2006 | Ashraf | |
| 2007/0141311 A1 | 6/2007 | Mleziva et al. | |
| 2008/0004583 A1 * | 1/2008 | Desai et al. | 604/385.01 |
| 2008/0253820 A1 | 10/2008 | Baba et al. | |
| 2009/0159187 A1 | 6/2009 | Ashraf | |

FOREIGN PATENT DOCUMENTS

| | | |
|---|---|---|
| JP | 2003-153946 A | 5/2003 |
| JP | 2006-27089 A | 2/2006 |
| WO | WO 2007/061486 | 5/2007 |

OTHER PUBLICATIONS

PCT International Search Report, PCT/US2010/038284 date of mailing Oct. 18, 2010.

* cited by examiner

*Primary Examiner* — Jacqueline Stephens
(74) *Attorney, Agent, or Firm* — Sarah M. DeCristofaro; Charles R. Ware (57) ABSTRACT

Stretched laminates with prestrained elastics.

18 Claims, 5 Drawing Sheets

PRESTRAINED STRETCHED LAMINATES

CROSS REFERENCE TO RELATED APPLICATIONS

This application claims the benefit of U.S. provisional patent application 61/186,689 filed Jun. 12, 2009, the substance of which is hereby incorporated by reference.

FIELD

In general, embodiments of the present disclosure relate to stretched laminates with prestrained elastics. In particular, embodiments of the present disclosure relate to stretched laminates with prestrained elongate elastic elements for use with disposable wearable absorbent articles.

BACKGROUND

Absorbent articles can absorb liquid bodily exudates such as sweat, blood, urine, menses, etc. An absorbent article can include elastic legbands and/or an elastic waistband. Unfortunately, some legbands and waistbands may have a rough plastic appearance or feel. Some integral legbands and waistbands may not appear finished and garment-like. And some legbands and waistbands that only use live stretch tend to use materials inefficiently. Also some legbands and waistbands may not adequately conform the article to a wearer's body. Absorbent articles with such legbands and waistbands may look unattractive, cost more, and perform poorly.

DETAILED DESCRIPTION

The embodiments of prestrained stretched laminate of the present disclosure can be used with all kinds of absorbent articles and disposable garments. An absorbent article can absorb liquid bodily exudates such as sweat, blood, urine, menses, etc. An absorbent article can be a product or a material. Examples of absorbent articles include products and/or materials for sanitary protection, hygienic use, and/or wound care. Some absorbent articles are disposable. A disposable absorbent article is configured to be partly or wholly disposed of after a single use. A disposable absorbent article is configured such that the soiled article, or a soiled portion of the article, is not intended to be restored and reused (e.g., not intended to be laundered). Examples of disposable absorbent articles include wound care products, such as bandages and dressings, as well as feminine care products, such as pads and liners. Disposable absorbent articles can use embodiments of the present disclosure.

Some absorbent articles are wearable. A wearable absorbent article is configured to be worn on or around a body of a wearer. Wearable absorbent articles can also be disposable. Examples of disposable wearable absorbent articles include disposable diapers and disposable incontinence undergarments. A disposable wearable absorbent article can receive and contain bodily exudates while being worn by a wearer. In some embodiments, a disposable wearable absorbent article can include a topsheet, an absorbent core, an outer cover, a waist opening, and leg openings. Disposable wearable absorbent articles can use embodiments of the present disclosure.

The embodiments of prestrained stretched laminates of the present disclosure can be used as a front waistband, back waistband, leg band, and/or anchoring band; embodiments can be used in or on a side ear, side panel, topsheet, outer cover, and/or other suitable portions of a wearable absorbent article, as described herein. Such prestrained stretched laminates can be attached to a wearable absorbent article as discrete pieces or continuous bands, on the wearer side, on the garment side, or interposed between layers of the article (e.g. integral).

The figures of the present disclosure are intended to illustrate elements, their parts, and their relationships, as described in the specification; the figures are not intended to illustrate any particular relative or absolute size or dimension, unless otherwise stated in the text.

Figure 1A:
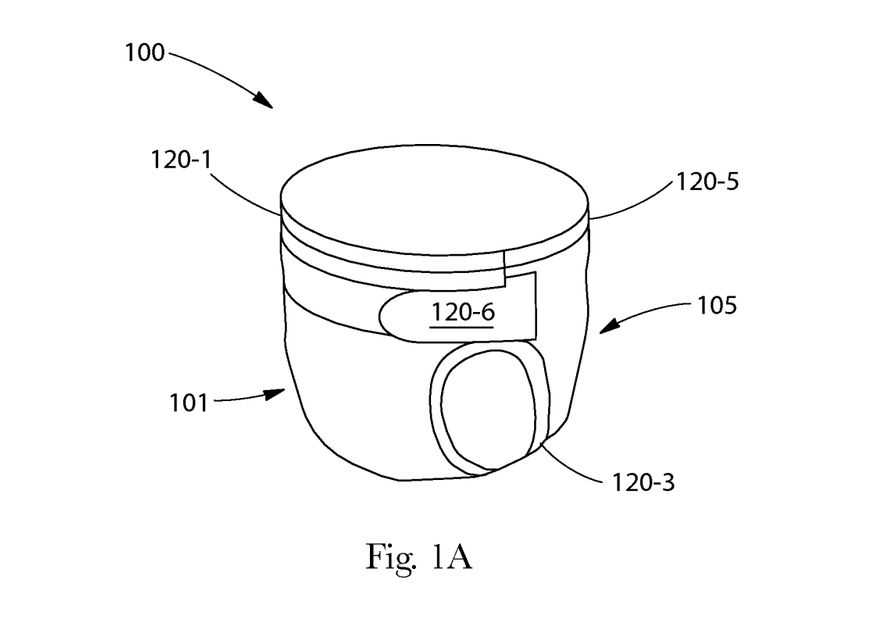
FIG. 1A illustrates a front outside perspective view of a front-fastenable wearable absorbent article formed for wearing, wherein the article includes legbands and waistbands, according to embodiments of the present disclosure.

FIG. 1A illustrates a front outside perspective view of a front-fastenable wearable absorbent article 100 formed for wearing. The article 100 has a front 101 and a back 105. The article includes a front waistband 120-1, legbands 120-3, a back waistband 120-5, and side ears 120-6. Any of the front waistband 120-1, legbands 120-3, back waistband 120-5, and side ears 120-6, or a portion thereof, can be configured to include or be formed from any of the embodiments of the prestrained stretched laminates of the present disclosure.

While the present disclosure refers to front-fastenable absorbent articles, the present disclosure also contemplates alternate embodiments of absorbent articles using prestrained stretched laminates, as described herein, wherein the absorbent articles are rear-fastenable or side fastenable. Thus, each embodiment of an absorbent article of the present disclosure that is described as front-fastenable can also be configured to be rear fastenable, as will be understood by one of ordinary skill in the art.

Figure 1B:
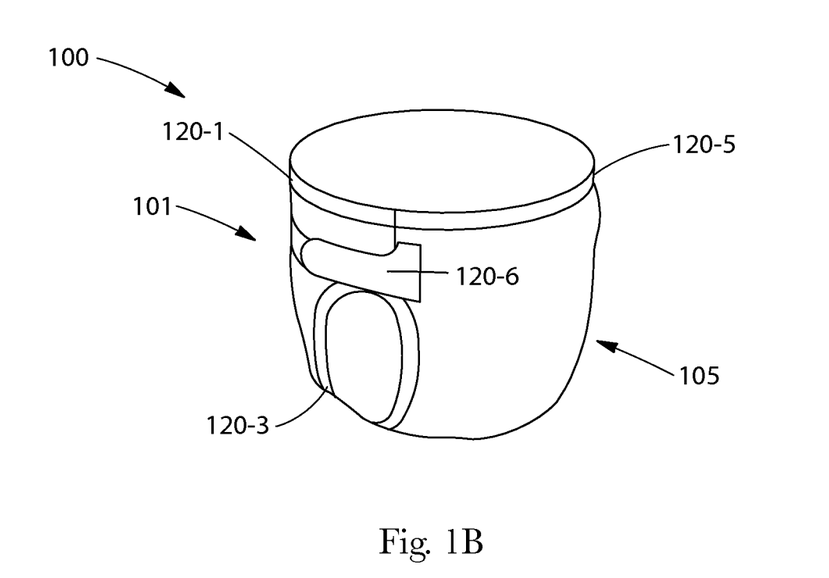
FIG. 1B illustrates a back outside perspective view of the article of the embodiment of FIG. 1A.

FIG. 1B illustrates a back outside perspective view of the article of the embodiment of FIG. 1A.

Figure 2A:
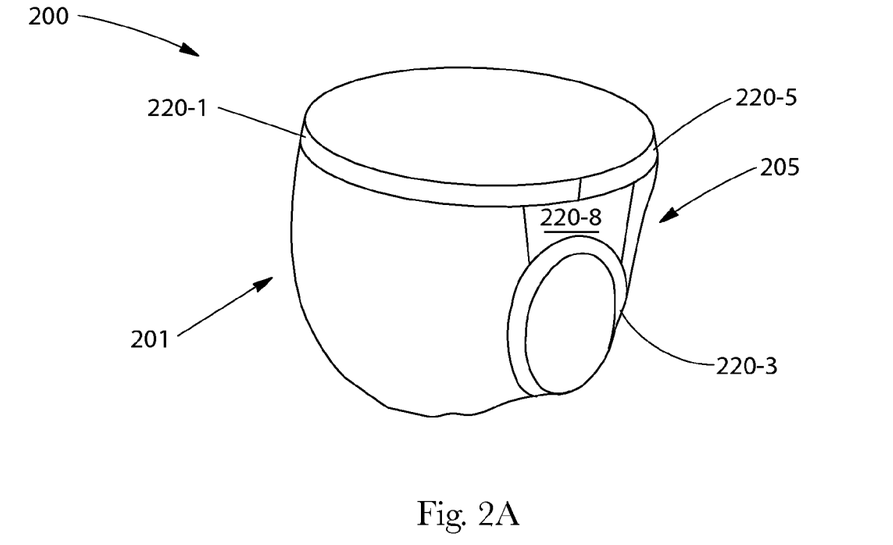
FIG. 2A illustrates a back outside perspective view of a pant-type wearable absorbent article formed for wearing, wherein the article includes legbands and waistbands, according to embodiments of the present disclosure.

FIG. 2A illustrates a back outside perspective view of a pant-type wearable absorbent article 200 formed for wearing. The article 200 has a front 201 and a back 205. The article includes a front waistband 220-1, legbands 220-3, a back waistband 220-5, and side panels 220-8. Any of the front waistband 220-1, legbands 220-3, back waistband 220-5, and side panels 220-8 can be configured to include or be formed from any of the embodiments of the prestrained stretched laminate of the present disclosure.

Throughout the present disclosure, a reference to a pant-type wearable absorbent article refers to an article with sufficient stretch to enable it to be readily pulled over a wearer's hips and buttocks while the waist and leg openings are formed. A pant-type wearable absorbent article can refer to an embodiment that is side-fastenable, to an embodiment that is front-fastenable or to an embodiment without fasteners. A reference to a pant-type wearable absorbent article can also refer to an article with preformed waist and/or leg openings or to an embodiment that is not preformed. Thus, each embodiment of an absorbent article of the present disclosure that is described as pant-type can be configured in any of these ways, as will be understood by one of ordinary skill in the art.

Figure 2B:
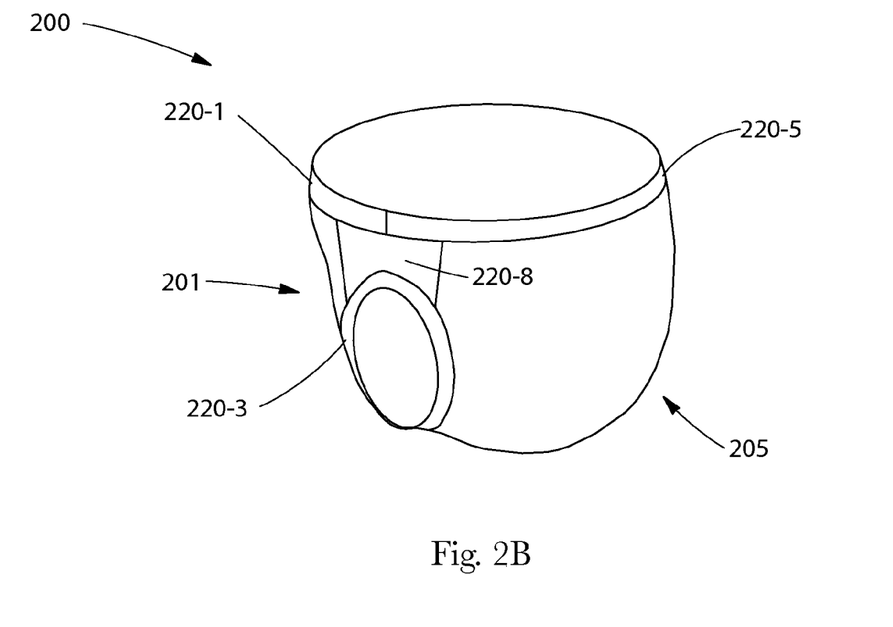
FIG. 2B illustrates a back outside perspective view of the article of the embodiment of FIG. 2A.

FIG. 2B illustrates a back outside perspective view of the article of the embodiment of FIG. 2A.

Figure 3A:
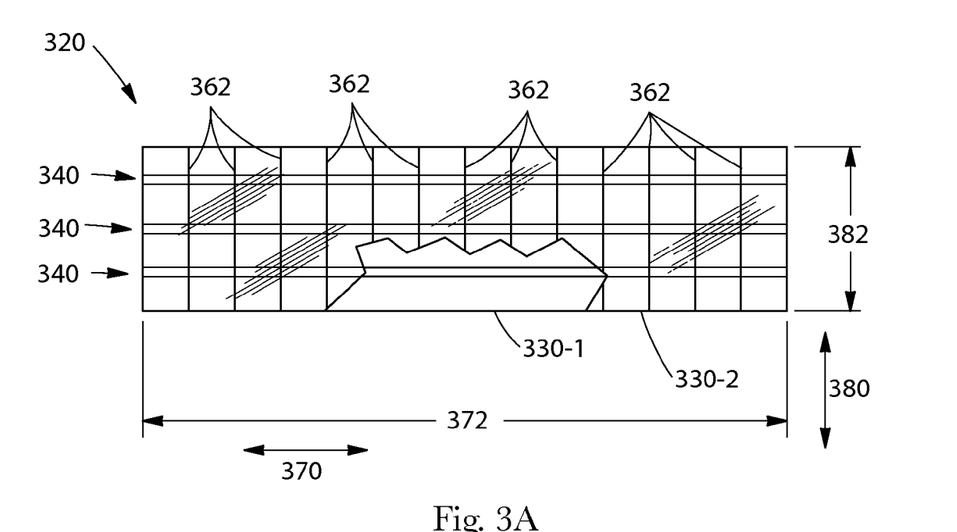
FIG. 3A illustrates a top view of a prestrained stretched laminate with elongate elastic elements, wherein the laminate is pulled flat, according to embodiments of the present disclosure.

FIG. 3A illustrates a top view of a prestrained stretched laminate 320. The prestrained stretched laminate 320 has a first inealastic layer 330-1 and a second inelastic layer 330-2. The first inelastic layer 330-1 is disposed subjacent to the second inelastic layer 330-2. In various embodiments, any of the embodiments of a prestrained stretched laminate of the present disclosure can also include one or more additional materials, such as additional layers.

The prestrained stretched laminate 320 also includes a plurality of elongate elastic element 340 disposed between the inelastic layers 330-1 and 330-2. As used herein, the term elongate elastic element is intended to refer to an element with a width greater than or equal its thickness, and a length much greater than its width, such as strands, ribbons, strips, and bands. In the embodiment of FIG. 3A, the elongate elastic element 340 are elastic strands. However, in various embodiments the elongate elastic element 340 can be other elongate elastic elements such as strands, ribbons, strips, and/or bands, or combinations thereof.

In FIG. 3A, the prestrained stretched laminate 320 is illustrated as if the prestrained stretched laminate 320 is pulled flat. The prestrained stretched laminate 320 has a primary direction 370 and a second direction 380 perpendicular to the primary direction 370. The first inelastic layer 330-1 and/or the second inelastic layer 330-2 has an inelastic extensibility in the primary direction 370. The prestrained stretched laminate 320 may or may not have an inelastic extensibility in the secondary direction 380 or in other directions.

As used herein, the term "extensible" refers to the property of a material (or a composite of multiple materials) that can extend, without substantial rupture or breakage, to 50% in the Hysteresis Test (as described herein). Micro-sized rupture or breakage of a material is not considered substantial rupture or breakage. However, macro-sized ruptures through the structure (e.g. one or more large tears such as tears greater than about 5 millimeters in any direction, or breaking into two or more pieces, or resulting in significant structural degradation which may render the material unusable for its intended purpose) are considered substantial ruptures or breakage. A material that does not meet this definition for "extensible" is considered "inextensible." An extensible material may be elastic or inelastic as defined herein.

As used herein, the term "elastic" refers to the property of an extensible material (or a composite of multiple materials) that can extend, without substantial rupture or breakage, to 50% in the Hysteresis Test, with a set less than or equal to 10% of the elongation as measured according to the Hysteresis Test. For example, a material that has an initial length of 25 millimeters and extends 12.5 millimeters to an extended length of 37.5 millimeters (50% elongation) with a set of 1 millimeter (8% of the elongation), when subjected to the Hysteresis Test, would be considered elastic. An elastic material is considered elastically extensible.

As used herein, the term "inelastic" refers to the property of an extensible material (or a composite of multiple materials) that can extend, without substantial rupture or breakage, to 50% in the Hysteresis Test, with a set greater than 10% of the elongation as measured according to the Hysteresis Test. For example, a material that has an initial length of 25 millimeters and extends 12.5 millimeters to an extended length of 37.5 millimeters (50% elongation) with a set of 2 millimeters (16% of the elongation), when subjected to the Hysteresis Test, would be considered inelastic. An elastic material is considered inelastically extensible.

In some materials, the properties of extensibility, elasticity, and inelasticity can be directional. That is a material may be extensible in a first direction, but not be extensible in a second direction. In these cases, the material's properties would be considered direction dependent. The material would be considered extensible in the first direction, but inextensible in the second direction. Similarly, a material's elasticity or inelasticity can also be described in terms of a particular direction within the material.

The first inelastic layer 330-1 and/or the second inelastic layer 330-2 can be a sheet of material formed from film (such as a polyolefin film), nonwoven, foam, scrim, a natural fiber (e.g. cotton), or combinations thereof. The sheet can be formed from one layer of material, or several layers of material, such as a laminate. As an example, inelastic layers can be a linear low density polyethylene film with a basis weight of 18 grains per square meter (gsm).

The first inelastic layer 330-1 and/or the second inelastic layer 330-2 can be formed from separate sheets or from a single sheet folded over onto itself. The first inelastic layer 330-1 and/or the second inelastic layer 330-2 can be liquid impermeable or liquid permeable. The first inelastic layer 330-1 and/or the second inelastic layer 330-2 can be vapor impermeable or vapor permeable. In various embodiments, the inelastic layers can be permeable by their construction, or rendered permeable by aperturing.

Each of the elongate elastic elements 340 has an elastic extensibility along its length. Each of the elongate elastic elements 340 is substantially parallel with the primary direction 370. As a result, each of the elongate elastic elements 340 provides elastic extensibility to the prestrained stretched laminate 320 in the primary direction 370. In various embodiments, the elongate elastic elements 340 can be completely parallel with the primary direction 370.

The elongate elastic elements 340 can be formed from various materials, such as Lycra, rubber, Spandex, styrene ethylbutylene styrene, styrene ethylene propylene styrene, styrene ethylene ethylene propylene styrene, styrene butadiene styrene, styrene isoprene styrene, polyolefin elastomers, elastomeric polyurethanes, rubbers, similar materials, and combinations thereof. In some embodiments, the elongate elastic elements 340 can be extruded strand elastics. As an example, the elongate elastic elements 340 can be 1240 decitex soft Spandex. In various embodiments, any or all of the elongate elastic elements 340 can have a decitex ranging from 540 to 1580, or any integer value for any decitex value in this range, or any range formed by any of these integer values.

As used herein, the term prestrained is intended to refer to one or more elastic elements in an extended state. Prestrain is measured from an initial length of the element, wherein the elastic element is under enough tension to remove any slack but not so much tension as to elastically extend the element. For example, when an elongate elastic element is prestrained 10%, the element is extended to 110% of its initial length.

Each of the elongate elastic elements 340 is attached to the inelastic layers 330-1 and 330-2 while prestrained at least 10% in the primary direction 370 relative to the inelastic layers 330-1 and 330-2, to form a precursor laminate of elastic and inelastic elements. This attachment of prestrained elastics can be accomplished in various ways. As a first example, while the inelastic layer is not extended, elongate elastic elements can be prestrained 10% and then applied to the inelastic layer. As a second example, while the elastic layer is extended, the elongate elastic elements can be prestrained to match the elastic layer's extension, plus prestrained an additional 10% and then applied to the inelastic layer.

In various embodiments, one or more of the elongate elastic elements 340 can be attached to the inelastic layers 330-1 and 330-2 at a prestrain of at least 10%, at least 25%, at least 50%, at least 75%, at least 100%, at least 150%, at least 200%, or any integer prestrain value among any of these percentages, or any range formed by any of these integer values. Each of the elongate elastic elements 340 can be attached at the same prestrain, or at differing prestrains. Alternatively, one or more of the elongate elastic elements 340 can be attached at zero or substantially zero prestrain.

As used herein, the term extended is intended to refer to one or more elastic and/or inelastic elements in an extended state. Extension is measured from an initial length of the element(s), wherein the element(s) are under enough tension to remove any slack but not so much tension as to inelastically extend any inelastic elements. For example, when a laminate of elastic and inelastic elements is extended 25%, the laminate is extended to 125% of its initial length. Extension is measured macroscopically (i.e. with respect to the overall length of the element(s)) and is not intended to measure local variations in extension, such as those caused by friction lock.

After the elongate elastic elements 340 are attached, the precursor laminate is extended at least 35% in the primary direction 370 to form the prestrained stretched laminate 320. It should be noted that, as part of this extension, the inelastic portion of the precursor laminate is extended inelastically. The extension can be accomplished in various ways, such as by stretching the laminate between several pairs of nip rolls with each pair running at a higher speed compared to the previous one, incremental stretching, or other activation techniques, such as ring-rolling. The extension process can be applied to the laminate while the laminate is in a relaxed state, while the laminate is under tension to remove slack, or while the laminate is under a process tension. It is contemplated that the extension process can be applied to the laminate before the laminate is attached to an article or after the laminate is attached to the article. In various embodiments, the extension can be accomplished using a profiled activation process, such as those described in US patent application entitled "Process for Activating a Web", filed Nov. 19, 2007 and published as US publication 20090127742.

In the embodiment of FIG. 3A, the prestrained stretched laminate 320 is illustrated as including a plurality of tooth marks 362 from an intermeshing of teeth in an activation-type stretching process. As an example, the extension can be accomplished with intermeshing teeth having 0.100" pitch, with a 2.7 millimeter depth of engagement. In various embodiments, the precursor laminate can be extended, in the primary direction, at least 50%, at least 75%, at least 100%, at least 150%, at least 200%, at least 250%, at least 300%, or any integer extension value among any of these percentages, or any range formed by any of these integer values. The precursor laminate may or may not be extended in the secondary direction 380, or any other direction, before or after attachment to an article.

When the prestrained stretched laminate 320 is under enough tension to remove any slack but not so much tension as to further inelastically extend the inelastic layers 330-1 and 330-2, the prestrained stretched laminate 320 has an overall extended length 372, measured in the primary direction 370, and an overall extended width 382, measured in the secondary direction 380. In the embodiment of FIG. 3A, the overall extended length 372 is much greater than the overall extended width 382, resulting in the prestrained stretched laminate 320 with an overall rectangular shape; however this is not required and the prestrained stretched laminate 320 can be configured in various other shapes, e.g. via curving the prestrained stretched laminate on an article or folding or cutting it to shape it.

For the prestrained stretched laminate 320, the overall extended width 382 is determined by the overall width of the inelastic layers 330-1 and 330-2. The overall extended width 382 is somewhat narrower than the original overall width of the inelastic layers 330-1 and 330-2, since the inelastic extension in the primary direction 370 may cause neckdown in the secondary direction 380. The amount of necking will depend on the properties of the inelastic layers 330-1 and 330-2 and the nature of the inelastic extension. As an example, the inelastic layers 3301- and 330-2 may experience necking that results in a 5-25% reduction in their overall width.

In various embodiments of waist and leg bands, the prestrained stretched laminate 320 can have an overall extended width 382 that is at least 5 millimeters, at least 10 millimeters, at least 15 millimeters, at least 20 millimeters, at least 30 millimeters, at least 40 millimeters, at least 50 millimeters, or any integer value in millimeters among any of these dimensions, or any range formed by any of these integer values. For a stretchable outer cover, a side ear, or a side panel made from a prestrained stretched laminate, these dimensions may be substantially larger; for example, a stretchable outer cover made from the laminate could have the dimensions of the full length and width of the diaper.

The prestrained stretched laminate 320 has a laminate elastic extensibility that is the product of the prestrain of the elongate elastic elements 340 producing a fore-shortened relaxed state and the inelastic extension induced in the inelastic layers, corrected for the small amount of set in the elastic material as it goes through these transformations. For example, in a prestrained stretched laminate where the elastics have been prestrained 10% and the inelastic layers have been extended of 25%, the laminate elastic extensibility is calculated at 1.10 times 1.25, yielding a result of 1.38, with the assumption that percent set is small and can be neglected; so the example prestrained stretched laminate would have a laminate elastic extensibility of 38%. Further examples are shown in Table 1, shown below.

TABLE 1

| | | \multicolumn{10}{c}{PRESTRAIN OF ELASTIC ELEMENTS} |
| | | 10% | 20% | 30% | 40% | 50% | 60% | 70% | 80% | 90% | 100% |
|---|---|---|---|---|---|---|---|---|---|---|---|
| EXTENSION | 20% | 32% | 44% | 56% | 68% | 80% | 92% | 104% | 116% | 128% | 140% |
| OF | 25% | 38% | 50% | 63% | 75% | 88% | 100% | 113% | 125% | 138% | 150% |
| INELASTIC | 30% | 43% | 56% | 69% | 82% | 95% | 108% | 121% | 134% | 147% | 160% |
| ELEMENTS | 40% | 54% | 68% | 82% | 96% | 110% | 124% | 138% | 152% | 166% | 180% |
| | 50% | 65% | 80% | 95% | 110% | 125% | 140% | 155% | 170% | 185% | 200% |
| | 60% | 76% | 92% | 108% | 124% | 140% | 156% | 172% | 188% | 204% | 220% |
| | 70% | 87% | 104% | 121% | 138% | 155% | 172% | 189% | 206% | 223% | 240% |
| | 80% | 98% | 116% | 134% | 152% | 170% | 188% | 206% | 224% | 242% | 260% |
| | 90% | 109% | 128% | 147% | 166% | 185% | 204% | 223% | 242% | 261% | 280% |
| | 100% | 120% | 140% | 160% | 180% | 200% | 220% | 240% | 260% | 280% | 300% |
| | 110% | 131% | 152% | 173% | 194% | 215% | 236% | 257% | 278% | 299% | 320% |
| | 120% | 142% | 164% | 186% | 208% | 230% | 252% | 274% | 296% | 318% | 340% |
| | 130% | 153% | 176% | 199% | 222% | 245% | 268% | 291% | 314% | 337% | 360% |
| | 140% | 164% | 188% | 212% | 236% | 260% | 284% | 308% | 332% | 356% | 380% |
| | 150% | 175% | 200% | 225% | 250% | 275% | 300% | 325% | 350% | 375% | 400% |
| | 160% | 186% | 212% | 238% | 264% | 290% | 316% | 342% | 368% | 394% | 420% |
| | 170% | 197% | 224% | 251% | 278% | 305% | 332% | 359% | 386% | 413% | 440% |
| | 180% | 208% | 236% | 264% | 292% | 320% | 348% | 376% | 404% | 432% | 460% |
| | 190% | 219% | 248% | 277% | 306% | 335% | 364% | 393% | 422% | 451% | 480% |
| | 200% | 230% | 260% | 290% | 320% | 350% | 380% | 410% | 440% | 470% | 500% |

It should be noted that the results in Table 1 are based on the assumption of no set. Any set would increase the initial dimension and thus reduce the elasticity of the prestrained stretched laminates.

In various embodiments, a prestrained stretched laminate can have a laminate elastic extensibility, in the primary direction, with elastic extensions of at least 35%, at least 50%, at least 100%, at least 200%, at least 300%, at least 400%, at least 500%, at least 600%, or any integer value among any of these percentages, or any range formed by any of these integer values.

Figure 3B:
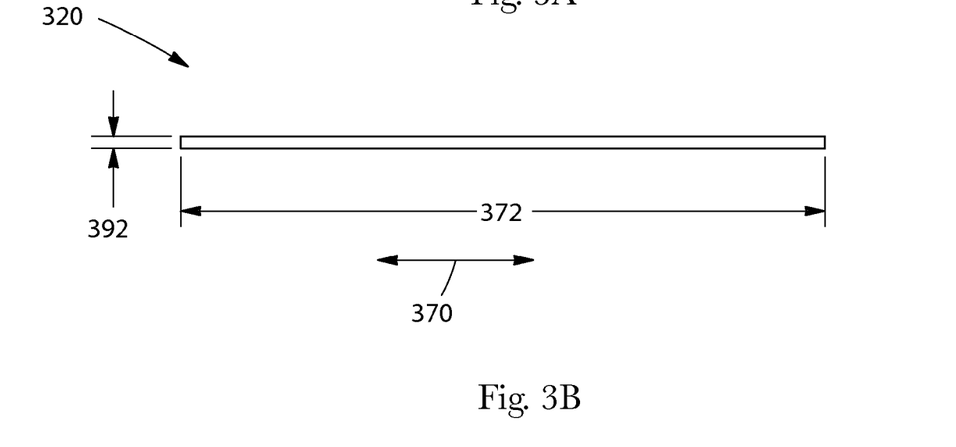
FIG. 3B illustrates a side view of the prestrained stretched laminate of the embodiment of FIG. 3A.

FIG. 3B illustrates a side view of the prestrained stretched laminate 320 of the embodiment of FIG. 3A. The prestrained stretched laminate has an overall extended thickness 392.

Figure 3C:
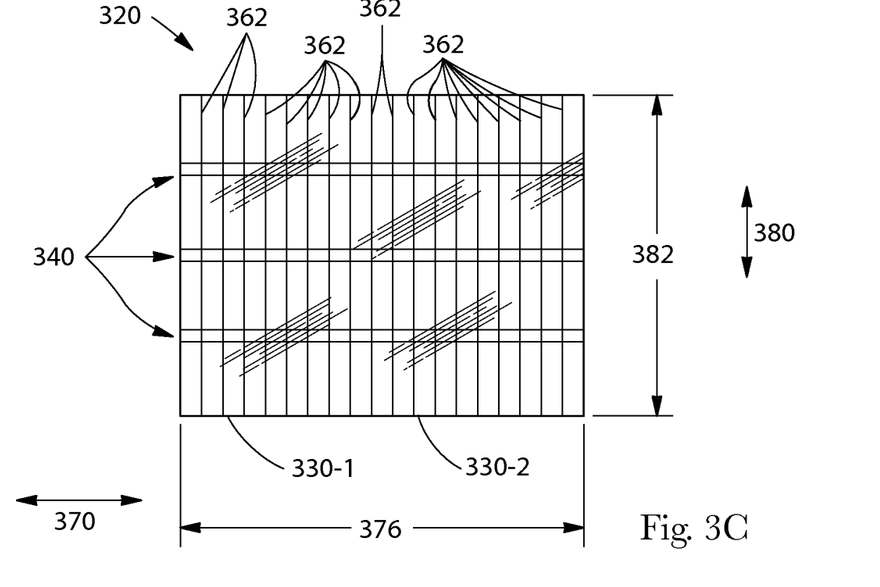
FIG. 3C illustrates a top view of the prestrained stretched laminate of the embodiment of FIG. 3A in a relaxed state, according to embodiments of the present disclosure.

FIG. 3C illustrates a top view of the prestrained stretched laminate 320 of the embodiment of FIG. 3A in a relaxed state (with the elongate elastic elements 340 contracting the prestrained stretched laminate 320) after the prestrained stretched laminate 320 has been extended in the primary direction 370. The prestrained stretched laminate 320 has an overall relaxed length 376 in the primary direction 370 and an overall relaxed width 386 in the secondary direction 380. Without wishing to be bound by this theory, it is believed that when the prestrained stretched laminate 320 is released from the extending process and the prestrained stretched laminate 320 is relieved of the forces causing the inelastic extension, the elongate elastic elements 340 contract the inelastic layers 330-1 and 330-2, which, in turn, buckle out of the plane defined by the primary direction 370 and the secondary direction 380, resulting in a plurality of shirrs 332, with each of the shins oriented in the secondary direction and contributing to an overall relaxed thickness 396 of the prestrained stretched laminate 320.

Figure 3D:
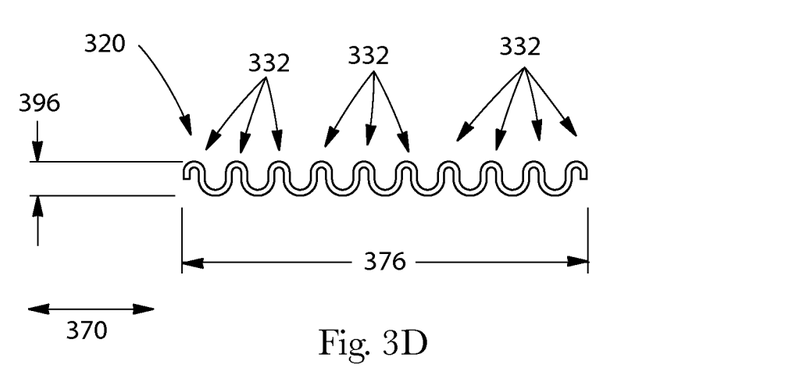
FIG. 3D illustrates a side view of the prestrained stretched laminate of the embodiment of FIG. 3C.

FIG. 3D illustrates a side view of the prestrained stretched laminate 320 of the embodiment of FIG. 3C. In some embodiments, the overall relaxed thickness 396 can vary from 1 mm, to 2 mm, to 3 mm, to 4 mm, to 5 mm, or larger. These measurements of overall relaxed thickness are taken under a pressure of 0.2 psi. This pressure is intended to flatten the relaxed prestrained stretched laminate without causing significant deformation and bending/collapsing of the shins. The shins 332 form a regular undulating pattern of shirrs alternating up and down, which tends to give the prestrained stretched laminate 320 a high-quality textile-like appearance. As a result, an absorbent article that includes the prestrained stretched laminate 320 can look attractive. The overall relaxed thickness 396 also gives the prestrained stretched laminate 320 a gentle resiliency to pressure applied from above the prestrained stretched laminate 320, which tends to give the prestrained stretched laminate 320 a soft feel. As a result, an absorbent article that includes the prestrained stretched laminate 320 can be tactilely pleasing. In various embodiments, either or both of the inelastic layers 330-1 and 330-2 can be treated with further processing, such as abrading, embossing, hydro-aperturing, vacuum-aperturing, and the addition of fibers, in order to further improve the soft feel of the outer surfaces of the prestrained stretched laminate 320. It is contemplated that any of these processes can be performed before or after the laminate is inelastically extended.

Despite the presence of the shirrs 332, the prestrained stretched laminate 320 as a whole still tends to lie flat in its relaxed state; that is, the prestrained stretched laminate 320 does not experience large scale buckling that causes the prestrained stretched laminate 320 as a whole to curl up off of a surface on which it is resting. This provides good processability for the prestrained stretched laminate 320. Without wishing to be bound by this theory, it is believed that the prestrained stretched laminate 320 can be configured to obtain a beneficial regular pattern of shins 332 without undesirable large scale buckling, by selecting appropriate spacings of the elongate elastic elements 340. Throughout the present disclosures, all spacing measurements for elongate elastic elements are measured to the center of the element. In some embodiments, the spacing between any two adjacent elongate elastic elements 340 can be selected from the group including 1 millimeter, 2 millimeters, 3 millimeters, 4 millimeters, 5 millimeters, 6 millimeters, or a greater distance or any range formed by any of these values.

In various embodiments, either or both of the first inelastic layer 330-1 and the second inelastic layer 330-2 can be white or can include a colored tinting of any color and any level of opacity. Either or both of the inelastic layers 330-1 and 330-2 can be transparent to reveal the underlying elongate elastic elements 340 and to create a visual effect of an elastic like waistband for the observer. One or more outer layers of a prestrained stretched laminate may also be printed to further enhance the appearance of softness and garment-like texture. Any of these design features may be combined with others to alter or enhance the appearance of the prestrained stretched laminate 320 and/or an absorbent article including such a laminate.

Also, one or more of the elongate elastic elements 340 can be white or can include a colored tinting, of any color. In some embodiments, the inelastic layers 330-1 and 330-2 and the elongate elastic elements 340 can have matching colors. In other embodiments, the inelastic layers 330-1 and 330-2 and the elongate elastic elements 340 can have contrasting colors. Such contrasting colors may be desirable, in order to simulate the appearance of a line of stitching in a cloth material. In various embodiments, the color of the inelastic layers 330-1 and 330-2 and/or the elongate elastic elements 340 may contrast or match other portions of an article to which the prestrained stretched laminate 320 is attached.

Figure 3E:
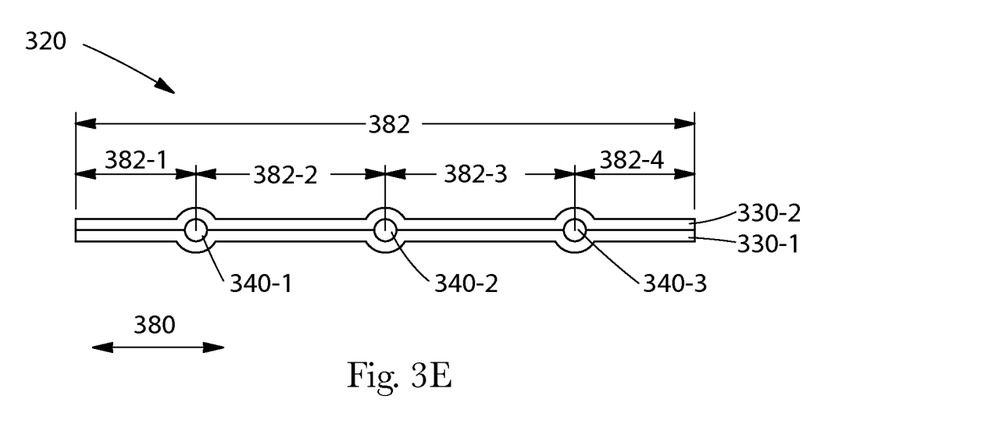
FIG. 3E illustrates an end view of the prestrained stretched laminate of the embodiment of FIG. 3A.

FIG. 3E illustrates an end view of the prestrained stretched laminate 320 of the embodiment of FIG. 3A. In the embodiment of FIG. 3E, the inelastic layers 330-1 and 330-2 are in contact with each other across the overall extended width 382, except where the contact is interrupted by the elongate elastic elements 340. In some embodiments, it may be desirable to affect a mechanical attachment between part or all of the inelastic layers 330-1 and 330-2. For example, the left side edge of the prestrained stretched laminate 320 or the right side edge of the prestrained stretched laminate 320, or both side edges may be sealed. The sealing may assist in keeping the elongate elastic elements 340 captured between the inelastic layers 330-1 and 330-2 and may also provide a more finished appearance to the prestrained stretched laminate 320. Alternatively, in one or more of the spaces between the elongate elastic elements 340 and/or the spaces between the elongate elastic elements 340 and the side edges, the inelastic layers 330-1 and 330-2 may be mechanically connected with various techniques, applied either to the prestrained stretched laminate 320 by itself or, applied as the prestrained stretched laminate 320 is being bonded to an absorbent article.

While the elongate elastic elements 340 are illustrated as elastic strands having a round cross-section, elongate elastic elements can have various cross-sectional shapes.

The plurality of elongate elastic elements 340 includes a first elastic strand 340-1, a second elastic strand 340-2, and a third elastic strand 340-3. However, in various embodiments, a prestrained stretched laminate 320 can include 1-10 strands, or any number of strands in this range.

The first elastic strand 340-1 is located a first spaced apart distance 382-1 in the secondary direction 380 from the left side edge of the prestrained stretched laminate 320. The second elastic strand 340-2 is located a second spaced apart distance 382-2 in the secondary direction 380 from the first elastic strand 340-1. The third elastic strand 340-3 is located a third spaced apart distance 382-3 in the secondary direction 380 from the second elastic strand 340-2. The third elastic strand 340-3 is also located a fourth spaced apart distance 382-4 in the secondary direction 380 from the right side edge of the prestrained stretched laminate 320.

The first spaced apart distance 382-1 may be the same as or different from the second spaced apart distance 382-4, and these distances can be selected from the group including 2 millimeters, 3 millimeters, 4 millimeters, 5 millimeters, 6 millimeters, or a greater distance, or any range formed by any of these values. Either or both of the spaced apart distances 382-1 and 382-4 may be the same as or different from either or both of the spaced apart distances 382-2 and 382-3. The spaced apart distance 382-2 may be the same as or different from the spaced apart distance 382-3, and can be selected from the group including 2 millimeters, 3 millimeters, 4 millimeters, 5 millimeters, 6 millimeters, 7 millimeters, 8 millimeters, 9 millimeters, 10 millimeters, or a greater distance, or any range formed by any of these integer values. Any of these distances can be uniform or varying. Any of these distances can be used with any other dimensions described herein.

Each of the elongate elastic elements 340 is attached to the inelastic layers 330-1 and 330-2. In the embodiment of FIG. 3E, each of the elongate elastic elements 340 is attached continuously along its length, however, in some embodiments, the attachment may be discontinuous. The attachment of the elongate elastic elements 340 can be accomplished in various ways. As an example, a slot coating of adhesive can be applied between the inelastic layers 330-1 and 330-2, and across all of the elongate elastic elements 340. As another example, adhesive can be slot coated onto the elongate elastic elements 340, with a slot for each of the elements. As a further example, adhesive can be applied as a spiral wrap on each of the elongate elastic elements 340. For instance, such adhesive spiral wraps can be applied with the SureWrap™ process using equipment available from the Nordson® Corporation. Also, adhesive can be applied using the Omega™ pattern from ITW®. As still a further example, the elongate elastic elements 340 can be coextruded with one or both of the inelastic layers 330-1 and 330-2. The present application contemplates that the elongate elastic elements 340 can also be attached in various other ways known in the art. These attachment techniques can be similarly applied to embodiments with elastic ribbons or sheets, as will be understood by one of skill in the art.

Figure 3F:
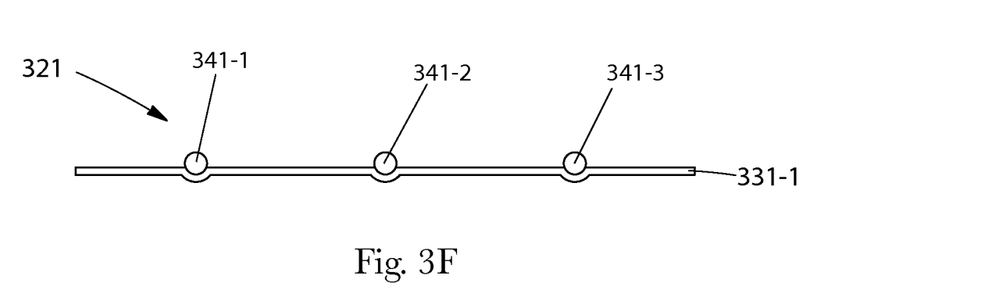
FIG. 3F illustrates an end view of an alternate embodiment of a prestrained stretched laminate, according to embodiments of the present disclosure.

FIG. 3F illustrates an end view of another alternate embodiment of a prestrained stretched laminate 321 in an extended state, according to embodiments of the present disclosure. The prestrained stretched laminate 321 of the embodiment of FIG. 3F is configured in the same way as the prestrained stretched laminate 320 of the embodiment of FIG. 3E, except that the prestrained stretched laminate 321 does not include a second inelastic layer. Otherwise, the prestrained stretched laminate 321 includes a first inelastic layer 331-1 configured in the same general way as the first inelastic layer 330-1 of the embodiment of FIG. 3E, and elastic strands 341-1, 341-2, and 341-3 are configured in the same general way as the elongate elastic elements 340-1, 340-2, and 340-3 of the embodiment of FIG. 3E.

As an example, a prestrained stretched laminate can include one inelastic layer that is combined with elongate elastic elements using a slot coat application of adhesive. In this embodiment, any exposed adhesive tack can be neutralized by the application of powders such as calcium carbonate or cornstarch. Any excess powder could be vacuumed off to create a single layer laminate. Alternatively, fibers (natural or synthetic) could be flocked to an adhesive layer coating just the elongate elastic elements or to the entire surface of a laminate with one inelastic layer.

Figure 3G:
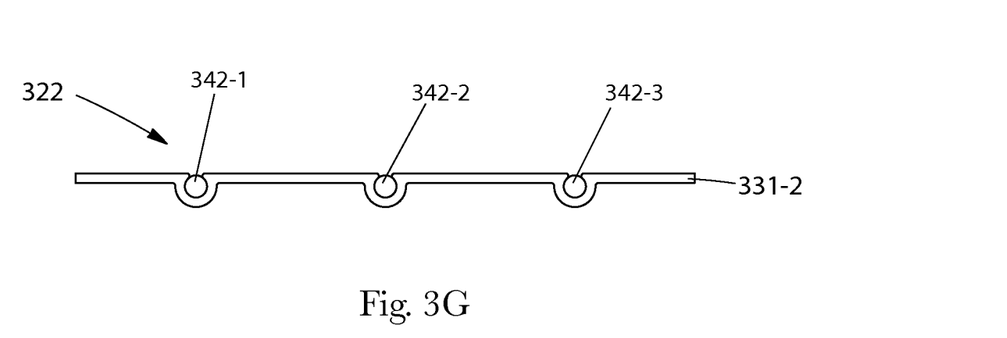
FIG. 3G illustrates an end view of another alternate embodiment of a prestrained stretched laminate, according to embodiments of the present disclosure.

FIG. 3G illustrates an end view of another alternate embodiment of a prestrained stretched laminate 322 in an extended state, according to embodiments of the present disclosure. The prestrained stretched laminate 322 of the embodiment of FIG. 3G is configured in the same way as the prestrained stretched laminate 321 of the embodiment of FIG. 3F, except that, in the prestrained stretched laminate 322, the elongate elastic elements are set within recessed portions formed within the inelastic layer 331-2. Otherwise, the prestrained stretched laminate 322 includes a first inelastic layer 331-2 configured in the same general way as the first inelastic layer 331-1 of the embodiment of FIG. 3F, and elastic strands

342-1, 342-2, and 342-3 are configured in the same general way as the elastic strands 341-1, 341-2, and 341-3 of the embodiment of FIG. 3F.

The embodiments of prestrained stretched laminates of the present disclosure can be attached to absorbent articles in various positions. An edge of a prestrained stretched laminate can coincide with part or all of an edge of a chassis of a wearable absorbent article. For example, when a prestrained stretched laminate is used as a waistband in a wearable absorbent article, an edge of the laminate can coincide with part or all of an edge of a chassis that forms a waist opening in the article. As another example, when a prestrained stretched laminate is used as a legband, an edge of the laminate can coincide with part or all of an edge of a chassis that forms a leg opening in the article. An edge of a prestrained stretched laminate can coincide with part or all of an edge of a wearable absorbent article by positioning the laminate with respect to the article, or by trimming the laminate (after the laminate is attached), or by trimming the laminate and the article together (after the laminate is attached). As an alternative example, when a prestrained stretched laminate is used as a legband, an edge of the laminate can extend out beyond part or all of an edge of a chassis that forms a leg opening in the article.

The embodiments of prestrained stretched laminates of the present disclosure can be attached to absorbent articles using various methods. For example, prestrained stretched laminates can be attached to wearable absorbent articles by using adhesive, ultrasonic bonding, bonding with heat and/or pressure, or other kinds of bonding, or combinations of any of these methods.

The embodiments of prestrained stretched laminates of the present disclosure can be used in front-fastenable and/or pant-type disposable wearable absorbent articles, as described below. In an exemplary embodiment, a pant-type disposable wearable absorbent article can include: an elastically extensible outer cover; a bucket-shaped core assembly including a liquid impermeable polyolefin film, a liquid permeable body side liner, and an absorbent core therebetween; a waist band; and leg bands. In variations of this exemplary embodiment, part, parts, substantially all, or all of the elastically extensible outer cover can be elastic. In a first variation, the article may be elastically extensible in a front waist region and a back waist region, but not in a crotch region. In a second variation, the article may be elastically extensible in its four side panel regions, but not in other regions. In a third variation, the article may be elastically extensible along one or more longitudinal stripes that run from the front of the article to the back of the article, but not in an area defined by the absorbent core.

Embodiments of a disposable wearable absorbent article of the present disclosure can include any of the various outer covers disclosed herein. A cloth-like outer cover may be a single layer of material or a laminate of two or more layers of material. The outer cover may include a base layer configured as an outer, wearer-facing side of the outer cover and the absorbent article. The base layer may be configured to be a relatively thin, low basis weight layer, which contributes to a relatively lightweight, thin outer cover. For example, the base layer may have a basis weight of between 10 and 50 g/m². The base layer may be configured to have a caliper of between 0.05 and 1 mm, under a pressure of 2100 Pascals. Calipers for both film and nonwoven materials described herein may be determined according to ASTM D5729-97 (2004), titled "Standard Test Method for Thickness of Nonwoven Fabrics." The base layer may be selected to provide a soft, cloth-like feel and may include one or more extensible nonwoven materials. For example, the base layer may be formed from a single layer of spunbond and/or meltblown polyolefin fibers (e.g., a polyethylene-containing nonwoven or any other suitable material known in the art). In certain embodiments, the base layer may include one or more webs of polypropylene/polyethylene blends. Blends of polyethylene and polypropylene may be provided in any suitable weight % based on the weight of the blend. For example, a blend may include weight percent ratios of 30/70, 50/50, 60/40, 70/30, 80/20 (polypropylene/polyethylene). The blends may be in the form of core/sheath-type bicomponent fibers (i.e., fibers that have an outer sheath of a first composition surrounding an inner core of a second composition) or side-by-side bicomponent fibers. Nonwovens made of polypropylene/polyethylene core/sheath bicomponent fibers may be configured to provide a web having a desired combination of softness, strength, and extensibility. The ratio of polypropylene and polyethylene in the core and sheath can be tailored to give the desired properties. One particularly suitable example of material for use as a soft, outer base layer is a spunbond nonwoven made from core/sheath type bicomponent fibers that include 70% polypropylene in the core and 30% polyethylene in the sheath, available from Fiberweb plc, Simpsonville, S.C. under the trade name SOFTEX. The base layer may also be a spunbond web comprising polypropylene or polyethylene monocomponent fibers. In another example, the base layer may be a spunbond-meltblown-spunbond polyolefin fibrous web that includes mono and/or bicomponent fibers. In yet another example, the base layer may include a monocomponent or bicomponent carded web.

The outer cover may also include an elastic layer. The elastic layer may be joined to the base layer by any means known in the art, e.g., adhesive bonding, ultrasonic bonding, thermal calendar bonding, high pressure bonding. The elastic layer may be intermittent (i.e., discontinuous) in one or more directions. For example, a longitudinally intermittent elastic layer may be present in a portion of one or both waist regions of the outer cover, but absent in at least a portion of the crotch region. In certain embodiments, the elastic layer may be coextensive with one or both waist regions in the longitudinal and/or lateral direction. In certain embodiments, the intermittent elastic layer may be formed from a single piece (or laminate) of elastic material that is substantially coextensive with only the body portion of one or both waist regions. In certain embodiments, a laterally intermittent elastic layer may be present in a portion of one or both side panel regions of an outer cover, but absent in at least a portion of the body region inboard of the side panel regions. In certain embodiments, the intermittent elastic layer may be both longitudinally and laterally intermittent. In certain embodiments, the elastic layer may be present as one or more elastic strips that extend laterally across the outer cover in a portion of one or both waist regions. The elastic layer may extend partially into the crotch region, however, it may be desirable to limit the extent to which the elastic layer extends into the crotch region to, e.g., limit the cost of producing the outer cover. The elastic layer may be exemplified as an elastic film, however, it is to be understood that the elastic layer may include one or more layers of elastic film(s), elastic nonwoven(s), and/or elastic strand(s), or laminates of elastic materials and extensible materials. For example, the elastic layer may be a bilaminate formed by joining the elastic layer to an extensible nonwoven layer, and then subjecting the bilaminate to an activation process to enable the laminate, for example, to stretch in at least the lateral direction. Alternatively or additionally, the bilaminate may be joined to the base layer and then subjected to an activation process. In another example, the elastic layer may be configured as a trilaminate, in which an elastic material layer is sandwiched between two extensible nonwoven layers, or between a nonwoven layer and a film layer. As with the bilaminate example, the trilaminate may be subjected to an activation process before, during, and/or after being joined to the base layer. Certain elastic materials suitable for use herein may have some amount of "tack" (i.e., stickiness), and thus may exhibit undesirable characteristics when wound onto and/or unwound from a roll (e.g., high unwind force and/or relatively noisy). In order to at least partially reduce the tendency of the tacky elastic material to stick to itself when wound onto a roll, another material (e.g., nontacky polymeric material) may be disposed on the surface(s) of the elastic material to act as a so-called "skin." The skin may at least partially mask the undesirable tackiness of the elastic material. It may be desirable to provide a relatively thin, lightweight outer cover, and therefore suitable basis weights for the elastic layer described herein may range from e.g., 10 to 100 grams per square meter ("gsm"), 15 to 75 gsm, or even 20 to 50 gsm. The skin basis weight may be from 2-10 gsm or 3-5 gsm. Suitable elastic layer calipers may range from, e.g., 0.01 to 0.1 mm. One particularly suitable example of an elastic material for use in the outer cover 500 is a 25 gsm elastic polypropylene film comprising VISTAMAXX, an elastomeric polypropylene resin available from ExxonMobil Chemical, Houston, Tex.

Because the elastic layer is generally not present in at least a portion of the crotch region of the outer cover, the structural integrity, opacity, and/or other characteristics of the outer cover in the crotch region may be undesirably impacted. To compensate for any such deficiencies, the basis weight of the outer cover base layer may be increased, but as pointed out above this may undesirable increase manufacturing costs and/ or diminish the clarity and vibrancy of the graphics. Therefore, it may instead be desirable to include a reinforcing member disposed generally in the crotch region of the outer cover, as disclosed in U.S. patent application Ser. No. 12/398, 615, filed on Mar. 5, 2009, entitled "Outer Cover for a Disposable Absorbent Article," which is hereby incorporated by reference. In various embodiments, bonding of the core bucket to a stretchable outer cover can be accomplished with a shaped bond area, as disclosed in U.S. patent application Ser. No. 12/468,633, filed on May 19, 2009, entitled "Attachment Areas for Wearable Absorbent Articles," which is hereby incorporated by reference.

Preparation of Samples for Hysteresis Test

To obtain a sample of an individual component (e.g. an elastic element or an inelastic layer) of a prestrained stretched laminate, when the component is available as separate material, prior to being attached to another component and/or formed in the laminate, cut each sample as described below. For sheet material, such as films and nonwovens used in an inelastic layer, cut each sample to be 5.5 cm long in the primary direction and the same width as the laminate when it is attached to the article. For elongate elastic elements, cut each sample to be 5.5 cm long, creating as many elongate elastic elements as there are in the prestrained stretched laminate. If the prestrained stretched laminate has different numbers of elongate elastic elements in different portions, then use the largest number of elongate elastic elements present in any of the portions. When placing the elongate elastic elements in the grips of the tensile tester the elements are placed adjacent to each other. When reporting the data for elongate elastic elements, use the laminate width, which is the width of the prestrained stretched laminate when it is attached to the article, to calculate load in N/cm.

To obtain a sample of an individual component of a prestrained stretched laminate, when the individual component is only available as part of the laminate attached to the chassis of a disposable wearable absorbent article, carefully remove each sample from the product, if possible, using any technique known to one skilled in the art. For example, if the laminate is adhered to the chassis, then freeze the adhesive bond and carefully peel the laminate from, the chassis, while taking care to ensure that layers of the laminate do not become separated from one another. Then, if possible, separate the elastic and inelastic elements. If it is not possible to separate a prestrained stretched laminate from a chassis or to separate elastic and inelastic elements without tearing or significantly damaging them, then those materials cannot be tested with this method.

To obtain a sample of a prestrained stretched laminate when the laminate is available as a separate structure, prior to being attached to the chassis of a disposable wearable absorbent article, cut each sample to be 5.5 cm long in the primary direction and the same width as the laminate when it is attached to the article.

To obtain a sample of a prestrained stretched laminate when the laminate is only available as attached to the chassis of a disposable wearable absorbent article, carefully remove each sample from the product, if possible, using any technique known to one skilled in the art. For example, if the laminate is adhered to the chassis, then freeze the adhesive bond and carefully peel the laminate from the chassis, while taking care to ensure that layers of the laminate do not get separated from one another. If it is not possible to separate a prestrained stretched laminate from a chassis without tearing or significantly damaging them (e.g. if the laminate is mechanically bonded to the chassis), then those materials cannot be tested with this method.

To obtain a sample of a prestrained stretched laminate in combination with a portion of the chassis underlying the prestrained stretched laminate, to which the laminate is attached, use one of the following procedures, depending on whether the laminate is used as a waist band or leg band.

When the prestrained stretched laminate is used as a waistband, to obtain a sample of the laminate in combination with the portion of the chassis, use one of the following procedures, as applicable. For a laminate that is a waistband on a pant-type disposable wearable absorbent article without fasteners and having a side seam, cut the article open at the side seam (cut in the middle for an overlap seam or cut along an inboard edge for a butt seam). For a laminate that is a waistband on a pant-type disposable wearable absorbent article without fasteners and having a front or back seam, cut the article open on the sides so that the width of the article in the front and in the back are the same. For a laminate that is a waistband on a front-fastenable disposable wearable absorbent article or on a refastenable pant-type disposable wearable absorbent article, wherein the fastener can be opened, open up the fasteners, and lay the opened article out with the outer cover facing upward and the topsheet facing downward (the article may or may not lie completely flat).

For each embodiment described above, to obtain a sample of the laminate as a waistband in combination with the portion of the chassis, use the following procedure. Without stretching the article, remove the entire back waistband from the chassis along with any portion of the chassis adhered to it. Accomplish this by cutting along the length of the waistband, ensuring that the sample is the same width as the prestrained stretched laminate. On the removed waistband, mark a line 15 mm laterally in from the terminal edge. Mark a second line 45 mm in from the terminal edge and cut the waistband along this line to obtain a sample 45 mm in length. If a 45 mm length is not available, a lesser length may be used, provided there is enough material to hold in the grips of the tensile tester at the 15 mm gauge length. Use this procedure to obtain two samples of the combination, one from each end of the removed waistband. If the length of the waistband is less than 90 mm, but greater than 45 mm, obtain samples from two separate articles, one from the right side, the other from the left.

When the prestrained stretched laminate is used as a legband, to obtain a sample of the laminate in combination with the portion of the chassis, use the following procedure. Without stretching the article, remove the entire legband from the chassis along with any portion of the chassis adhered to it. Accomplish this by cutting along the length of the legband, ensuring that the sample is the same width as the prestrained stretched laminate. On the removed legband identify the midpoint along the length of the sample. Measuring from the midpoint, mark a line 22.5 mm to both sides of this midpoint. Measuring from one of these lines towards the midpoint, mark a third line at 15 mm. Cut along the first two lines to obtain a sample 45 mm in length. Repeat this procedure for the other legband, to obtain two samples of the combination from the article.

Hysteresis Test

The Hysteresis Test can be used to various specified strain values, as described herein. The Hysteresis Test utilizes a commercial tensile tester (e.g., from Intron Engineering Corp. (Canton, Mass.), SINTECH-MTS Systems Corporation (Eden Prairie, Minn.) or equivalent) interfaced with a computer. The computer is used to control the test speed and other test parameters and for collecting, calculating, and reporting the data. The tests are performed under laboratory conditions of 23° C.±2° C. and relative humidity of 50%±2%. The samples are conditioned for 24 hours prior to testing.

Test Protocol

1. Select the appropriate jaws and load cell. The jaws must have flat surfaces and must be wide enough to fit the sample (e.g., at least 2.54 cm wide). Also, the jaws should provide adequate force to ensure that the sample does not slip during testing. The load cell is selected so that the tensile response from the sample tested is between 25% and 75% of the capacity of the load cell used.

2. Calibrate the tester according to the manufacturer's instructions.

3. Set the distance between the grips (gauge length). For a prestrained stretched laminate or components thereof, the distance is 25 mm. For a prestrained stretched laminate in combination with an underlying portion of a chassis, the distance is 15 mm.

4. Place the sample in the flat surface of the jaws such that the primary direction of the sample is substantially parallel to the gauge length direction. Mount the sample in the upper grip, let the sample hang slack, then close the lower grip. For the combination samples removed from an article, mount the sample such that the 15 mm line on the sample is aligned with the bottom edge of the upper grip. For elongate elastic elements, take as many elements as there are in the laminate sample, place them adjacent to each other, and grip them in between the jaws of the tensile tester. Set the slack preload at 0.02 N/cm. This means that the data collection starts when the slack is removed (at a constant crosshead speed of 10 mm/min) with a force of 0.02 N/cm. Strain is calculated based on the adjusted gauge length ($l_{ini}$), which is the length of the sample in between the grips of the tensile tester at a force of 0.02 N/cm. This adjusted gauge length is taken as the initial sample length, and it corresponds to a strain of 0%. Percent strain at any point in the test is defined as the change in length divided by the adjusted gauge length times 100.

6(a). First cycle loading: Pull the sample to the specified strain at a constant cross head speed of 100 min/min., Report the stretched sample length between the jaws as $l_{max}$.

6(b). First cycle unloading: Hold the sample at the specified strain for 30 seconds and then return the crosshead to its starting position (0% strain or initial sample length, $l_{ini}$) at a constant cross head speed of 100 mm/min. Hold the sample in the unstained state for 1 minute.

6(c). Second cycle loading: Pull the sample to the specified strain at a constant cross head speed of 100 mm/min.

6(d). Second cycle unload: Next, return the crosshead to its starting position (i.e. 0% strain) at a constant cross head speed of 100 mm/min.

A computer data system records the force exerted on the sample during the test as a function of applied strain. From the resulting data generated, the following quantities are reported (note that loads are reported as force divided by the width of the sample and do not take into account the thickness of the sample):

1. Length of sample between the grips at a slack preload of 0.02 N/cm ($l_{ini}$) to the nearest 0.001 mm.

2. Length of sample between the grips on first cycle at the specified strain ($l_{max}$) to the nearest 0.001 mm.

3. Length of sample between the grips at a second cycle load force of 0.02 N/cm ($l_{ext}$) to the nearest 0.001 mm.

4. % set, which is defined as $(l_{ext}-l_{ini})/(l_{max}-l_{ini})*100\%$ to the nearest 0.01%. The testing is repeated for six separate samples and the average and standard deviation reported.

Dimension Method

Various dimensions and ratios thereof are specified herein. Each dimension is measured according to the following method. All testing is performed in a conditioned room maintained at about 23 C±2 C and about 50%±2% relative humidity. Herein, width and length of the specimen are a lateral width and longitudinal length as defined herein. Precondition specimens at about 23 C±2 C and about 50%±2% relative humidity for 2 hours prior to testing.

Prepare the article for testing as follows:

1. Lay the article on a substantially flat, horizontal surface.

2. Secure the article to the surface such that all process-induced contraction acting to forshorten the absorbent core assembly is pulled out. For example, a pre-contracted waistband applied to the article or elastics along the longitudinal edges of the article and/or the absorbent core assembled may forshorten the article laterally or respectively longitudinally, so any such process-induced contraction is pulled out. The article is secured to the flat, horizontal surface with clamps or adhesive tape capable of holding the absorbent core assembly with process-induced contraction pulled out.

3. Identify points between which widths and/or lengths of each attachment region, the absorbent core assembly, any unattached areas, and the article are to be measured, per definitions contained herein. This includes defining the hip region.

4. Measure each needed dimension to the nearest 1 mm using a steel ruler traceable to NIST.

5. Calculate any needed ratios as follows: Ratio=100%× [First Measurement/Second Measurement].

Test Data

Samples 1-6, described below, were tested according to the Test Protocol of the Hysteresis Test with 50% as the specified stain (variations noted below) and the resulting percent set is reported in Table 2. Each of the Samples 1-6 was obtained as described in the Preparation of Samples section, above.

Sample 1 is a portion of a disposable wearable absorbent article comprising an elastic outer cover, an externally attached waistband that is a prestrained stretched laminate of the present disclosure, a bucket-shaped absorbent core assembly, and overlap seams on the sides. Sample 1 is the prestrained stretch laminate of the waistband in combination with a portion of the chassis. Four samples of Sample 1 were tested.

Sample 2 is a portion of a disposable wearable absorbent article comprising an elastic outer cover, an externally attached legband that is a prestrained stretched laminate of the present disclosure, a bucket-shaped absorbent core assembly, and overlap seams on the sides. Sample 2 is the prestrained stretch laminate of the legband in combination with a portion of the chassis. Four samples of Sample 2 were tested.

Sample 3 is a portion of the prestrained stretched laminate that is used in the waistband and legband of Samples 1 and 2. The Sample 3 laminate is 15 mm wide and has three strands of 1240 decitex Soft Spandex laminated between two layers of a polyethylene film obtained from Clopay, Mason, Ohio. This lamination was done with 1.5 mg/m/strand of H2401 adhesive obtained from Bostik, Wauwatosa, Wis., using the SureWrap glue application procedure. Three samples of Sample 3 were tested.

Sample 4 comprises the strands used in Samples 1, 2, and 3. Three samples of Sample 4 were tested.

Sample 5 is the polyethylene film (18 gsm) used in Samples 1, 2, and 3. Three samples of Sample 5 were tested.

Sample 6 is a portion of another prestrained stretched laminate. The Sample 6 laminate is 15 mm wide and has 3 strands of 1100 decitex Spandex laminated between two layers of a polyethylene film obtained from Swanson Plastics, China. This lamination was done with 1.5 mg/m/strand of H2401 adhesive obtained from Bostik, Wauwatosa, Wis., using the SureWrap glue application procedure. Three samples of Sample 6 were tested.

Sample 7 is the polyethylene film (24 gsm) was used in Sample 6. Three samples of Sample 7 were tested.

TABLE 2

| Sample | Percent Set | |
|---|---|---|
| | Mean | Std. dev. |
| 1 | 4.0 | 1.1 |
| 2 | 5.0 | 1.3 |
| 3 | 2.5 | 0.0 |
| 4 | 2.9 | 0.5 |
| 5 | 13.9 | 0.7 |
| 6 | | |
| 7 | 11.1 | 0.1 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a prestrained stretched laminate, comprising:
    prestraining at least one elongate elastic element at least 10% in a primary direction to form a prestrained elongate elastic element;
    attaching the prestrained elongate elastic element, while the elongate elastic element is prestrained, to an inelastic layer to form a precursor laminate; and
    extending the precursor laminate at least 35% in the primary direction to form the prestrained stretched laminate, wherein the inelastic layer of the precursor laminate is extended inelastically.

2. The process of claim 1, wherein the prestraining includes prestraining the at least one elongate elastic element at least 50% in the primary direction to form the prestrained elongate elastic element.

3. The process of claim 1, wherein the prestraining includes prestraining the at least one elongate elastic element at least 100% in the primary direction to form the prestrained elongate elastic element.

4. The process of claim 1, wherein the prestrained elongate elastic element is one of a plurality of elongate elastic element and the prestraining includes prestraining the plurality of elongate elastic element.

5. The process of claim 1, wherein the extending includes extending the precursor laminate at least 33% in the primary direction to form the prestrained stretched laminate.

6. The process of claim 1, wherein the extending includes extending the precursor laminate at least 50% in the primary direction to form the prestrained stretched laminate.

7. The process of claim 1, wherein the extending includes extending the precursor laminate at least 100% in the primary direction to form the prestrained stretched laminate.

8. The process of claim 1, wherein the extending includes extending the precursor laminate at least 200% in the primary direction to form the prestrained stretched laminate.

9. The process of claim 1, wherein the inelastic layer is a first inelastic layer and the attaching includes attaching the prestrained elongate elastic element, while the elongate elastic element is prestrained, to a second inelastic layer to form the precursor laminate.

10. The process of claim 1, wherein the prestrained stretch laminate is configured to be at least one of a leg band and a waist band.

11. The process of claim 1, wherein the prestrained stretch laminate comprises an overall relaxed thickness from greater than about 1 mm.

12. The process of claim 1, wherein the prestrained stretch laminate comprises shirrs.

13. The process of claim 1, further comprising the step of attaching the prestrained stretch laminate to a chassis of an absorbent article.

14. The process of claim 1, wherein the inelastic layer is a nonwoven.

15. The process of claim 1, wherein the inelastic layer is a film.

16. A process for making a prestrained stretched laminate, comprising:
- prestraining at least one elongate elastic element at least 10% in a primary direction to form a prestrained elongate elastic element;
- attaching the prestrained elongate elastic element, while the elongate elastic element is prestrained, to a first inelastic layer and a second inelastic layer to form a precursor laminate; and
- extending the precursor laminate at least 35% in the primary direction to form the prestrained stretched laminate, wherein the first inelastic layer and the second inelastic layer of the precursor laminate are extended inelastically.

17. The process of claim 16, wherein the first inelastic layer is at least one of a nonwoven and a film.

18. The process of claim 17, wherein the second inelastic layer is at least one of a nonwoven and a film.

* * * * *